United States Patent [19]

Gabbay et al.

[11] 4,372,747

[45] Feb. 8, 1983

[54] GLYCOHEMOGLOBIN DETERMINATION

[75] Inventors: Kenneth Gabbay, Chestnut Hill; Paul M. Gallop, Chestnut, both of Mass.

[73] Assignee: Children's Hospital Medical Center, Boston, Mass.

[21] Appl. No.: 288,777

[22] Filed: Jul. 31, 1981

[51] Int. Cl.³ .................. G01N 33/72; G01N 33/66; G01N 33/52

[52] U.S. Cl. .................. 436/67; 252/408.1

[58] Field of Search .................. 23/230 B, 913

[56] References Cited

U.S. PATENT DOCUMENTS 4,268,270  5/1981  Gabbay .................. 23/230 B

OTHER PUBLICATIONS

Belman (1963) Analytica Chimica Acta 29, 120–126.
Rahbar (1968) Clin. Chim. Acta 22, 296–298.
Trivelli et al. (1971) N. Eng. J. Med. 284, 353–357.
Gabbay et al. (1977) J. Clin. Endocrin, Metab. 44, 859–864.
Fluckiger et al. (1976) FEBS Lett. 71, 356–360.
Massamiri et al. (1978) Anal. Bioch. 91, 618–625.
Gabbay et al. (1978) American Society for Clinical Investigation, San Francisco, Cal.
Bunn et al. (1978) American Society of Biological Chemists.
Bunn et al. (1976) J. Clin. Invest. 57, 1652–1659.
Bunn et al. (1975) Biochem. Biophys. Res. Comm. 67, 103–109.
Bunn et al. (1978) Science 250, 21–27.

*Primary Examiner*—Sidney Marantz

[57] ABSTRACT

A method of measuring glycosylated hemoglobin featuring, in one aspect, providing a sample containing hemoglobin, including an unknown amount of glycosylated hemoglobin, contacting the sample with an oxidizing agent to generate formaldehyde, and measuring the formaldehyde as a measure of glycosylated hemoglobin, the measuring being carried out by reacting the formaldehyde with a water-soluble amine or an ammonium salt and a β-diketone to generate a fluorescent compound whose fluorescence is measured as a measure of glycosylated hemoglobin.

7 Claims, 2 Drawing Figures

GLYCOHEMOGLOBIN DETERMINATION

BACKGROUND OF THE INVENTION

The work described herein was supported in part by a grant or award from the National Institutes of Health.

This invention relates to the measurement of blood sugar levels.

There is described in Gabbay et al. U.S. Pat. No. 4,268,270, hereby incorporated by reference, a method of measuring glycosylated hemoglobin, which method includes providing a sample containing hemoglobin, including an unknown quantity of glycosylated hemoglobin, contacting the sample with an oxidizing agent to generate formaldehyde, and measuring the formaldehyde so generated as a measure of the unknown quantity of glycosylated hemoglobin.

SUMMARY OF THE INVENTION

In general, the invention features improved embodiments of the method described above, one such embodiment being the reaction of the formaldehyde with a water-soluble amine and a β-diketone to generate a fluorescent compound whose fluorescence is then measured as a measure of glycosylated hemoglobin. Preferably, the amine is ammonium acetate and the β-diketone is acetylacetone, which are most preferably combined, prior to reacting them with the formaldehyde, to form a formaldehyde detection reagent which is about 0.2 M ammonium acetate and about 0.02 M acetylacetone.

In another aspect, the invention features the step, prior to the oxidizing step, of removing hemin from the sample and precipitating globin by contacting the sample with tetrahydrofuran (THF), which is preferably mixed with an acid, and is most preferably about 1% in 12 N HCl.

In another aspect, the oxidizing agent is periodate, and any excess periodate is removed using zinc sulfate.

The invention provides a reliable measure of glycogroups in hemoglobin, and also provides resistance to variation caused by contaminated reagents.

Other advantages and features of the invention will be apparent from the following description of the preferred embodiment thereof, and from the claims.

DESCRIPTION OF THE PREFERRED EMBODIMENT

We turn now to a description of the preferred embodiment, first briefly describing the drawings.

DRAWINGS

EMBODIMENT

Figure 1:
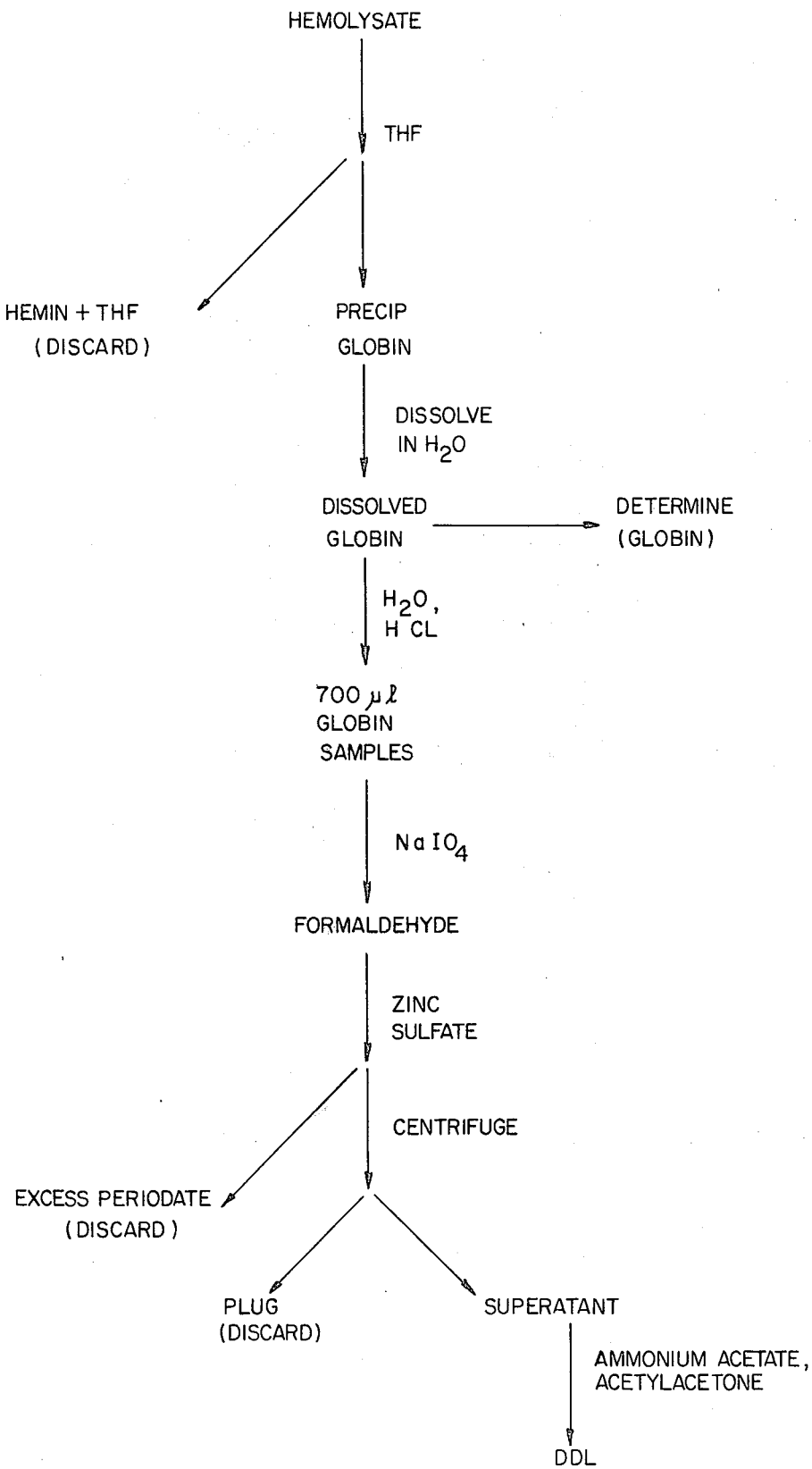
FIG. 1 is a flow diagram for a method of determining glycogroup equivalents in hemoglobin.

Referring to the flow diagram of FIG. 1, blood samples are collected in EDTA tubes, and erythrocytes are then separated from plasma by centrifugation ($1000 \times g$ for 10 minutes). The erythrocytes are washed three times with cold 0.9% saline, and hemolyzed by the addition of 4 volumes of cold distilled water. The red blood cell ghosts are removed by centrifugation ($20,000 \times g$, 10 min., 4° C.).

One ml of hemolysate is added dropwise to 10 ml freshly prepared cold acid THF (1 percent in 12 N HCl) with vortexing to remove hemin and to precipitate globin. The globin is then centrifuged ($1000 \times g$, 5 min.) and washed at least twice with 5 ml THF. If necessary, washing of the globin is continued until the globin is of a light buff color. The THF is then decanted, and the globin dissolved in 1-2 ml $H_2O$. Globin is measured in a Beckman model 135 spectrophotometer at 280 nm, with the calculation based on the percent extinction coefficient, according to the equation $E_{1\%} = 8.5$. All manipulations involving the use of THF are performed in a hood, and the test tubes are capped for centrifugation.

The volume of each sample aliquot containing 2-4 mg globin is adjusted to 700 μl with $H_2O$ and 20 μl 1 N HCl is then added. Oxidation to generate formaldehyde is then begun by the addition of 100 μl 0.1 N (14 nM) $NaIO_4$, pH 3.0, and allowed to proceed at room temperature for 30 minutes. The samples are then cooled on ice, and 300 μl of ice-cold 10% zinc sulfate and 100 μl of 1.4 N NaOH are added to remove excess periodate which might otherwise interfere with the measurement of formaldehyde. The samples are centrifuged ($1000 \times g$, 10 min.) and the supernatant containing formaldehyde collected. One ml of freshly prepared formaldehyde detection reagent (2 M ammonium acetate and 0.02 M acetylacetone) is added to initate the Hatzsch reaction, described in Belman (1963), Analytica Chimica Acta 29, 120-126, which results in the formation of the fluorescent compound 3,5-diacetyl-1, 4-dihydrolutidine (DDL). Fluorescence is allowed to develop for 1 hour at 37° C., pH 6.4. Fluorescence is determined by excitation at 410 nm and emission at 510 nm in an Aminco-Bowman 768F Spectrofluorometer equipped with a Schoeffel M460 photometer.

Figure 2:
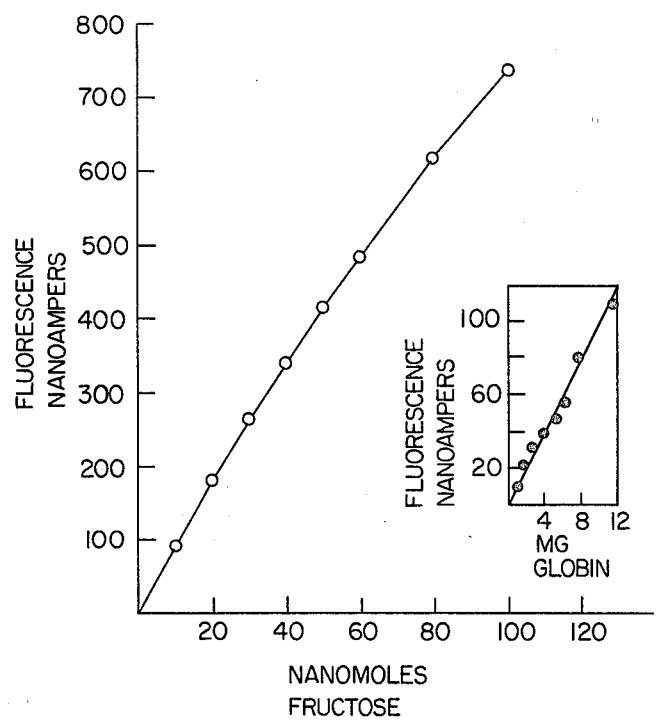
FIG. 2 is a standard fructose curve and an insert graph of the relation between fluorescence and globin concentration.
Figure 2:
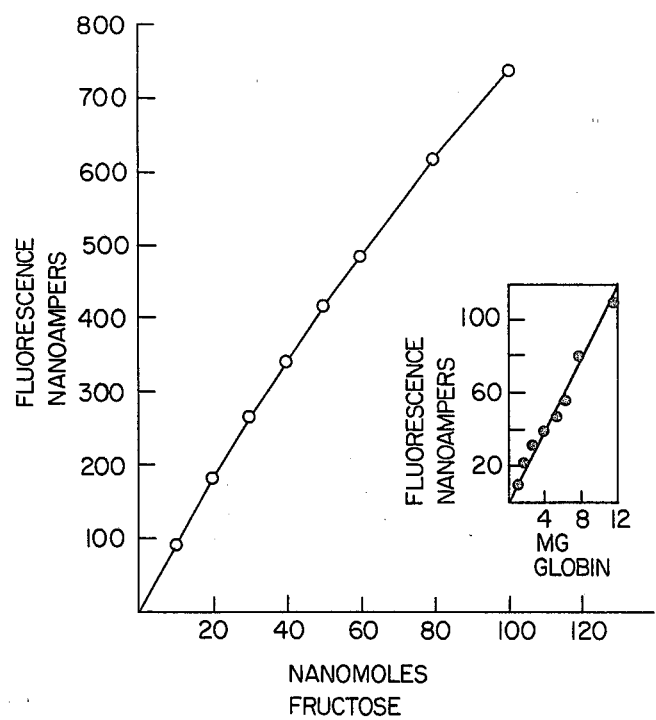

A fructose standard curve (10-40 nanomoles), as shown in FIG. 2, is simultaneously run with each assay. The fructose equivalents of formaldehyde are determined from the standard fructose curved by linear regression analysis and expressed as glycogroups/αβ-dimer according to the equation:

$$\frac{\text{glycogroups}}{\alpha\beta\text{-dimer}} = \frac{\text{nanomoles formaldehyde equivalents} \times 0.032}{\text{mg globin}}$$

The insert graph of FIG. 2 shows that formaldehyde released and measured as described above increases linearly with protein concentration from 1 to 12 mg globin. Because fluorescence yield deviates slightly from linearity at fructose concentrations greater than 40 nanomoles, the slope of the standard fructose curve of FIG. 2 is calculated from values up to 40 nanomoles fructose.

The above procedure produces reliable results which are unaffected by variable contamination by hemin or by slight impurities in the deionized water used. The method also gives a precise measure of the glycogroup content of hemoglobin samples.

OTHER EMBODIMENTS

Other embodiments are within the following claims. For example, measurable fluorescent compounds can be generated by reacting the formaldehyde produced by oxidation with any water soluble amine, e.g., other ammonium salts such as ammonium sulfate and ammonium chloride, and any β-diketone, e.g., benzoyl acetone or dibenzoyl methane, provided that the amine and the β-diketone form a fluorescent compound when reacted with formaldehyde. The general reaction is:

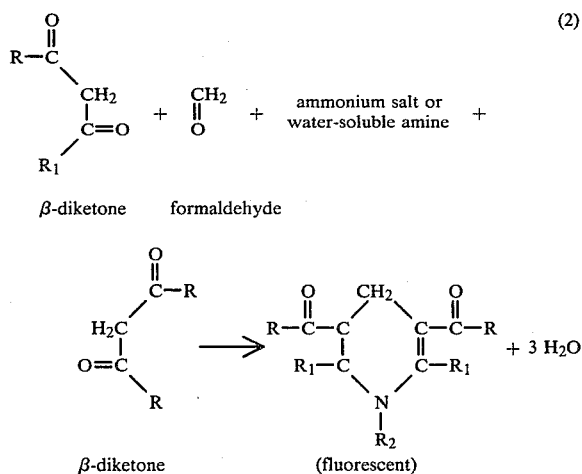

β-diketone (fluorescent)

wherein each R, $R_1$ is hydrogen or an alkyl or aryl group.

Oxidation can be carried out using any salt of periodic acid, or using other suitable oxidizing agent such as lead tetraacetate. When periodate is used, the concentration can vary widely, e.g., from 1 to 30 nM, or even higher, without appreciably affecting the generation of formaldehyde. The pH at which formaldehyde is generated can also vary, e.g., between about 5.5 and 6.5.

The amine and β-diketone concentrations can also vary somewhat, and the two need not be mixed together prior to their addition. The THF used to remove hemin can be made acidic by combining it with any non-interfering acid.

We claim:

1. A method of measuring glycosylated hemoglobin comprising
    providing a sample containing hemoglobin including an unknown quantity of glycosylated hemoglobin,
    contacting said sample with an oxidizing agent to generate formaldehyde, and
    measuring said formaldehyde as a measure of said unknown quantity of glycosylated hemoglobin,
    said measuring being carried out by reacting said formaldehyde with a water-soluble amine or an ammonium salt and a β-diketone to generate a fluorescent compound, the fluorescence of which is measured as a measure of said glycosylated hemoglobin.

2. The method of claim 1 wherein said ammonium salt is ammonium acetate and said β-diketone is acetylacetone.

3. The method of claim 2 wherein said ammonium acetate and said acetylacetone are combined, prior to reacting them with said formaldehyde, to form a formaldehyde detection reagent which is about 2 M ammonium acetate and about 0.02 M acetylacetone.

4. A method of measuring glycosylated hemoglobin comprising
    providing a sample containing hemoglobin including an unknown quantity of glycosylated hemoglobin,
    contacting said sample with tetrahydrofuran to remove hemin and precipitate globin,
    contacting said globin with an oxidizing agent to generate formaldehyde, and
    measuring said formaldehyde as a measure of said unknown quantity of glycosylated hemoglobin.

5. The method of claim 4 wherein said tetrahydrofuran is mixed with an acid.

6. The method of claim 5 wherein said tetrahydrofuran is about 1% in about 12 N HCl.

7. A method of measuring glycosylated hemoglobin comprising
    providing a sample containing hemoglobin including an unknown quantity of glycosylated hemoglobin,
    contacting said sample with periodate to generate formaldehyde,
    contacting said sample with zinc sulfate to remove excess periodate, and
    measuring said formaldehyde as a measure of said unknown quantity of glycosylated hemoglobin.

* * * * *